United States Patent
White

(10) Patent No.: US 11,460,385 B2
(45) Date of Patent: Oct. 4, 2022

(54) COMPACTION CONTROL SYSTEM FOR AND METHODS OF ACCURATELY DETERMINING PROPERTIES OF COMPACTED AND/OR EXISTING GROUND MATERIALS

(71) Applicant: Ingios Geotechnics, Inc., Northfield, MN (US)

(72) Inventor: David J. White, Northfield, MN (US)

(73) Assignee: Ingios Geotechnics, Inc., Northfield, MN (US)

( * ) Notice: Subject to any disclaimer, the term of this patent is extended or adjusted under 35 U.S.C. 154(b) by 131 days.

(21) Appl. No.: 16/787,395

(22) Filed: Feb. 11, 2020

(65) Prior Publication Data

US 2020/0256775 A1    Aug. 13, 2020

Related U.S. Application Data

(60) Provisional application No. 62/803,914, filed on Feb. 11, 2019.

(51) Int. Cl.
| | |
|---|---|
| *E01C 19/28* | (2006.01) |
| *G01N 3/14* | (2006.01) |
| *G01N 33/24* | (2006.01) |
| *G01N 33/42* | (2006.01) |

(52) U.S. Cl.
CPC .............. *G01N 3/14* (2013.01); *E01C 19/288* (2013.01); *G01N 33/24* (2013.01); *G01N 33/42* (2013.01); *E01C 19/282* (2013.01)

(58) Field of Classification Search
CPC .......... G01N 3/14; G01N 33/22; G01N 33/24; E01C 19/282; E01C 19/286

USPC .................. 404/72, 75, 84.05–84.5, 113, 117
See application file for complete search history.

(56) References Cited

U.S. PATENT DOCUMENTS

| | | | | |
|---|---|---|---|---|
| 5,727,900 | A * | 3/1998 | Sandstrom ............ | E01C 19/288 404/122 |
| 6,244,102 | B1 * | 6/2001 | Novak .................. | E01C 19/288 73/594 |
| 6,431,790 | B1 * | 8/2002 | Anderegg ............. | E01C 19/288 366/116 |
| 7,089,823 | B2 * | 8/2006 | Potts ..................... | E01C 19/288 404/117 |
| 8,112,242 | B2 * | 2/2012 | Troxler ................. | E01C 19/00 702/127 |
| 8,671,760 | B2 * | 3/2014 | Wallrath ................ | E02D 1/022 73/594 |

(Continued)

*Primary Examiner* — Raymond W Addie
(74) *Attorney, Agent, or Firm* — E. Eric Mills; Todd A. Serbin; Nexsen Pruet, PLLC

(57) ABSTRACT

A compaction control system for and methods of accurately determining properties of compacted and/or existing ground materials. The compaction control system includes a compaction machine that further includes a vibratory drum (or roller). The compaction machine is equipped with sensors to determine position and heading, vibration amplitudes at selected frequencies, and material type and moisture content information. Further, the compaction control system includes a controller and certain algorithms for processing the sensor information. Namely, a method is provided of using the sensor information to assess the improvement in compaction and then determine whether and/or when further ground improvement solutions are needed.

16 Claims, 11 Drawing Sheets

(56) References Cited

U.S. PATENT DOCUMENTS

| | | | |
|---|---|---|---|
| 10,145,837 B2* | 12/2018 | Troxler | G01N 33/246 |
| 10,301,781 B2* | 5/2019 | Laugwitz | G01N 29/12 |
| 2007/0276602 A1* | 11/2007 | Anderegg | E02D 3/046 |
| | | | 702/2 |
| 2009/0126953 A1* | 5/2009 | Anderegg | E02D 3/074 |
| | | | 172/1 |
| 2019/0094202 A1* | 3/2019 | Troxler | G01N 9/24 |

* cited by examiner

US 11,460,385 B2

COMPACTION CONTROL SYSTEM FOR AND METHODS OF ACCURATELY DETERMINING PROPERTIES OF COMPACTED AND/OR EXISTING GROUND MATERIALS

CROSS REFERENCE TO RELATED APPLICATION

This application claims the benefit of and priority to U.S. Provisional Patent Application No. 62/803,914 filed Feb. 11, 2019, and titled COMPACTION CONTROL SYSTEM FOR AND METHODS OF ACCURATELY DETERMINING PROPERTIES OF COMPACTED AND/OR EXISTING GROUND MATERIALS; the entirety of which is incorporated by reference herein.

TECHNICAL FIELD

The presently disclosed subject matter relates generally to measurement, analysis, design verification, and control of the spatial uniformity of engineering properties for compacted materials and existing ground and more particularly to a compaction control system for and methods of accurately determining properties of compacted and/or existing ground materials.

BACKGROUND

In situ testing and evaluation of engineered/compacted ground is often required to verify that pavement systems and structures built on the ground meet the requirements for providing adequate stiffness support and spatial uniformity of support. Traditional methods for constructing engineered ground is compaction of soil or aggregate built-up in layers with heavy rollers and incorporating chemical and mechanical stabilization materials with the soil or aggregate materials. The traditional method of verification that the ground is adequately constructed is normally limited to determining the density (weight-volume relationship) or stiffness (stress-deformation relationship) at discrete point locations. The discrete test point locations represent very limited coverage (often much less than one percent of the project area) that can lead to erroneous and grossly over-simplistic results when applied to the compacted continuum.

More recently, sensors have been integrated into compaction machines to determine the response of the roller-ground interactions. In one example, U.S. Pat. No. 5,493,494, entitled "Method and apparatus for operating compacting machinery relative to a work site," describes a system in which Global Positioning System (GPS) gauges are mounted on a roller compactor to measure the vertical elevation of the roller at a given location. This elevation is then measured during successive roller passes to provide a measure of compaction achieved. In another example, U.S. Patent Pub. No. 20070239338, entitled "Worksite preparation method using compaction response and mapping information," describes a system wherein a roller compactor is outfitted with sensors that measure rolling resistance, radiation gages, or fuel consumption that provide an indicator of the compaction achieved in a given work area. That relative compaction is then compared to other work areas to provide a relative indicator of compaction achievement. In yet another example, U.S. Pat. No. 8,635,903, entitled "Method and system for compaction measurement," describes a system whereby a roller compactor is outfitted with GPS gages and equipped with two compaction measurement systems, such as measuring the rolling resistance of the roller during compaction and measuring the accelerations of the drum during compaction, and providing an output display of the two measurements corresponding to compaction at different depths.

Although these prior systems provide an efficient means to collect data over a greater coverage area of the project, existing roller-ground measurement values are applied without consideration of local site conditions and do not provide a practical or robust means of determining material stiffness. The existing systems are further flawed by exhibiting large variations in the measured results and poor accuracy. For these reasons, practitioners lack confidence in these devices, causing the existing methods to only be narrowly deployed and almost always on a purely experimental basis. The existing methods are further limited by an inability to accurately determine soil moisture content values or material consistency (soil type), measurements that are needed by engineers and constructors to determine material response and to verify that the compacted soil type has not changed in consistency. The existing devices and systems also do not improve the spatial uniformity of engineering design values.

It is well understood in geotechnical engineering practice that non-uniform stiffness and compressibility contributes to undesirable stress concentrations, reduced service life, differential settlement, and other problems for the overlying pavement systems/structures. Therefore, new approaches are needed for robustly determining soil stiffness with suitable accuracy for commercial use and for determining soil moisture content and consistency. New approaches are needed that can be used in real time by constructors to reduce the variability of the compacted material stiffness and that can be used by engineers and constructors as a means for determining locations for remediation and/or for providing an overall quality control platform. Additionally, new approaches are needed that thoroughly document the thickness and stiffness of the compacted layers.

SUMMARY

The invention provides a method for the efficient determination of geospatial characterization of design engineering values for compacted materials to determine areas of noncompliance that can require rework/improvement and changes to the construction process to improve spatial uniformity. Pavement systems, earthen dams and dikes, embankments and structure-supporting earth fills that are constructed without uniformly achieving adequate density and stiffness are prone to performance issues including non-uniform settlement, excessive stresses in underlying layers, the potential for seepage-induced "piping" and eventually failure. The present subject matter is particularly effective at improving the quality of ground and compacted fill because it provides spatially-significant and accurate measurements of stiffness and, optionally moisture content and consistency, thereby providing determinations of relevant engineering properties in real-time. The present subject matter provides visual records of results using integrated sensors and algorithms to calibrate the results to independent test results. The present subject matter further optionally allows for real-time determinations of areas that must be remediated and assessments of the overall quality achieved. The present subject matter further serves as a robust inspection and documentation tool by providing spatially-indexed maps of stiffness and compacted material thickness.

In one embodiment, the present subject matter consists of an apparatus and system for accurately determining relevant compaction material properties, such as material stiffness, in spatially significant scale and real time visualization of the collected information. In a second embodiment, the present subject matter provides a system for the selection of the material response calibration locations. In a third embodiment, the present subject matter provides a means for achieving great accuracy in the determination of measured values. In yet another embodiment, the present subject matter allows the for the determination of soil moisture content values and material type using measurements of color and intensity. In another embodiment, the present subject matter allows for the creation of resilient modulus (stiffness) curves for increasing compaction effort. In another embodiment, the present subject matter provides a means to visualize the measurements in real time, communicate the measurements to off-site personnel, and to determine zones that require remediation. In another embodiment the present subject matter provides for a robust inspection and documentation tool by providing maps of material stiffness and compacted material thickness.

BRIEF DESCRIPTION OF DRAWINGS

Figure 1:
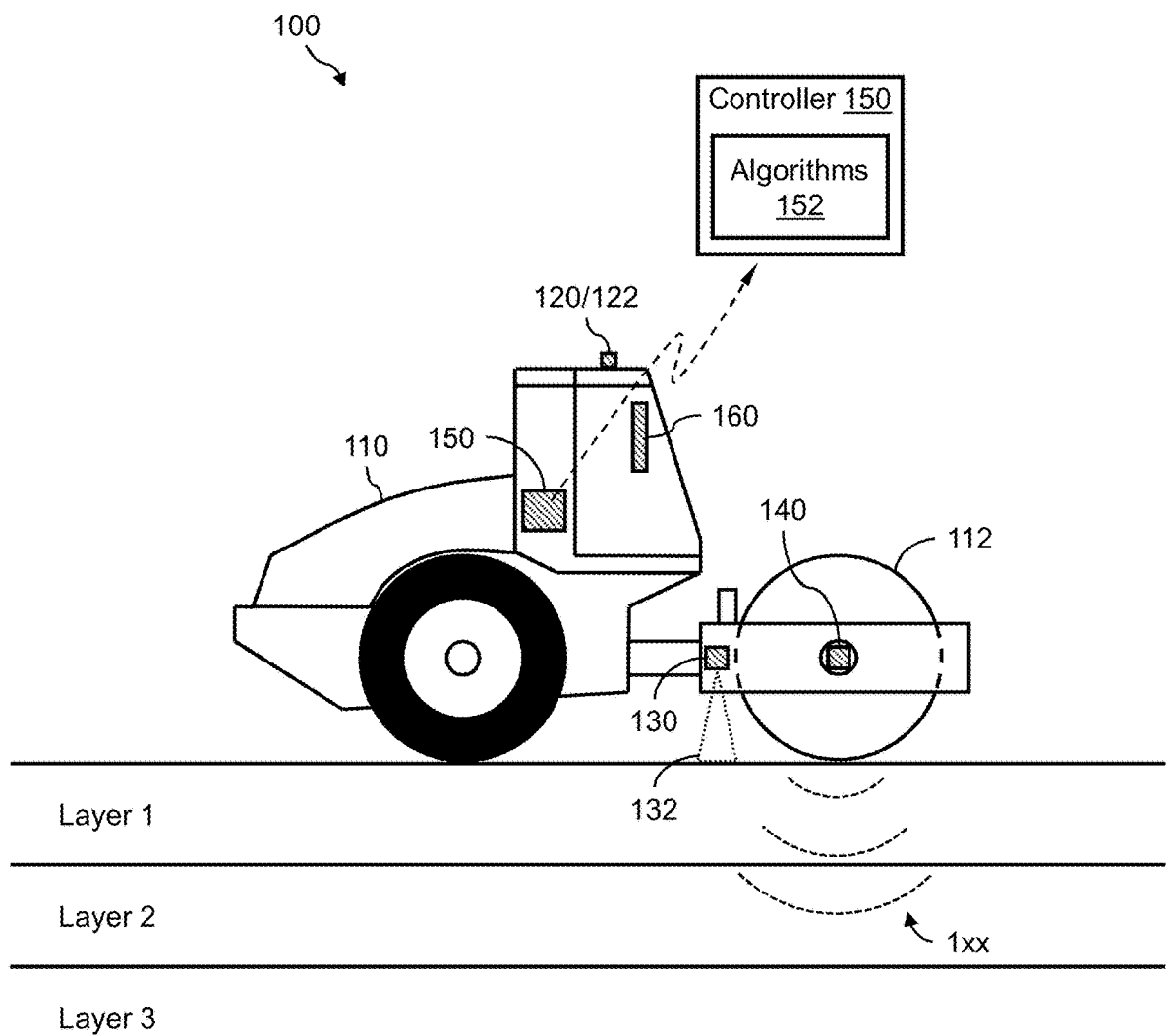
Figure 2:
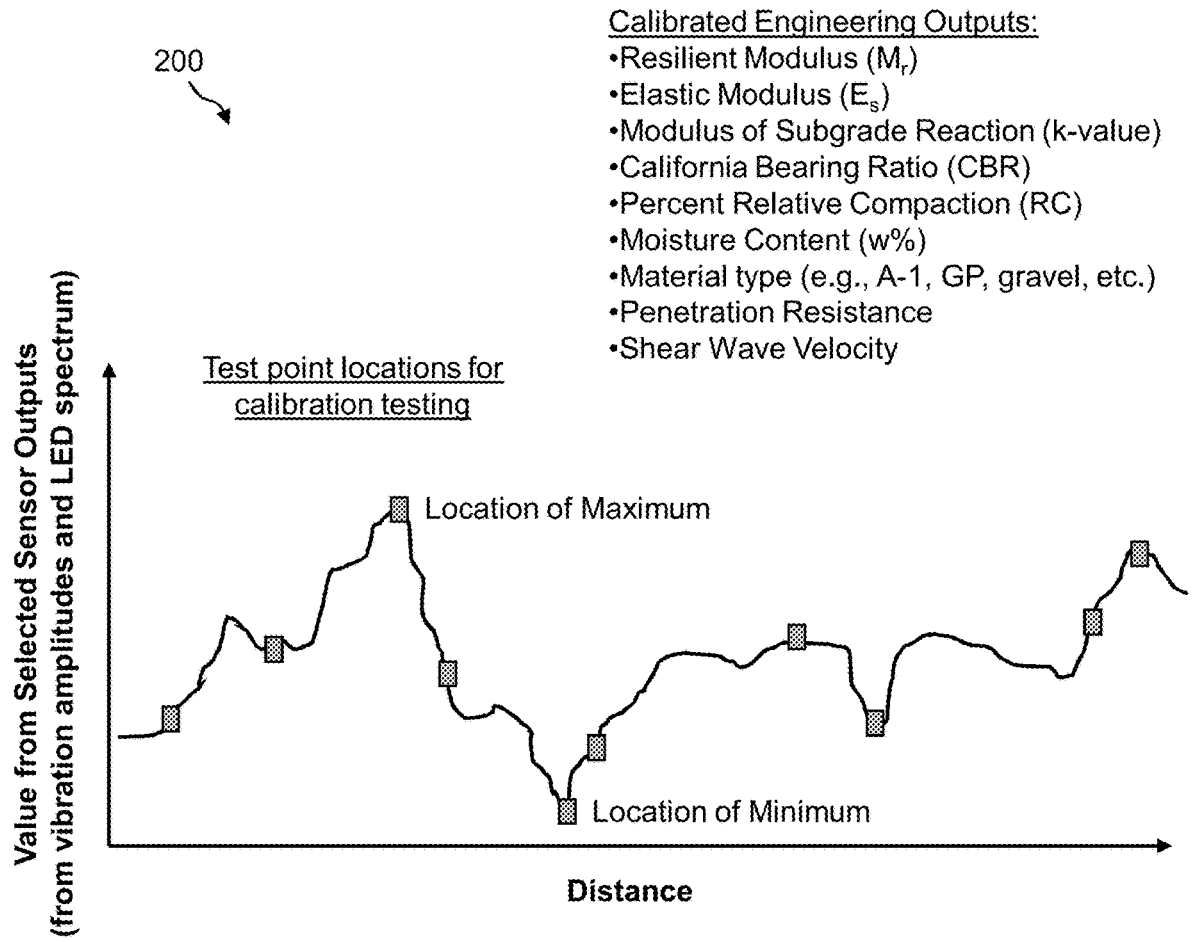
Figure 3:
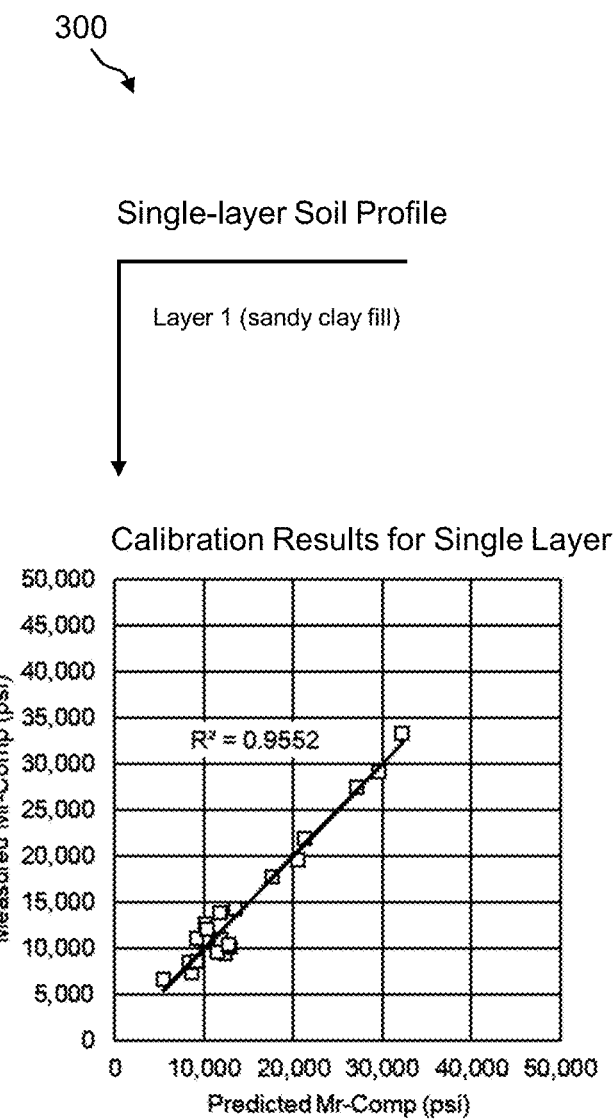
Figure 4:
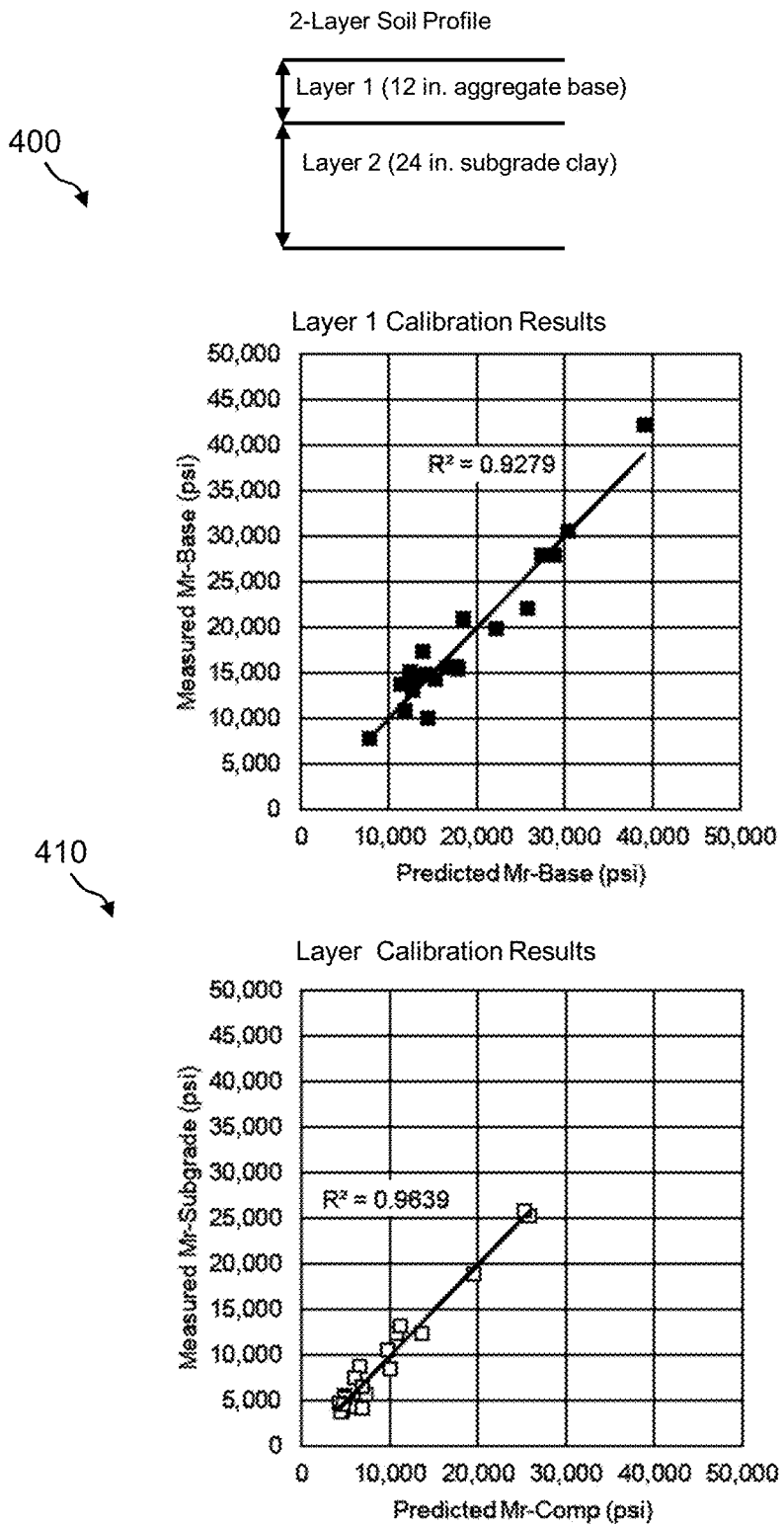
Figure 5:
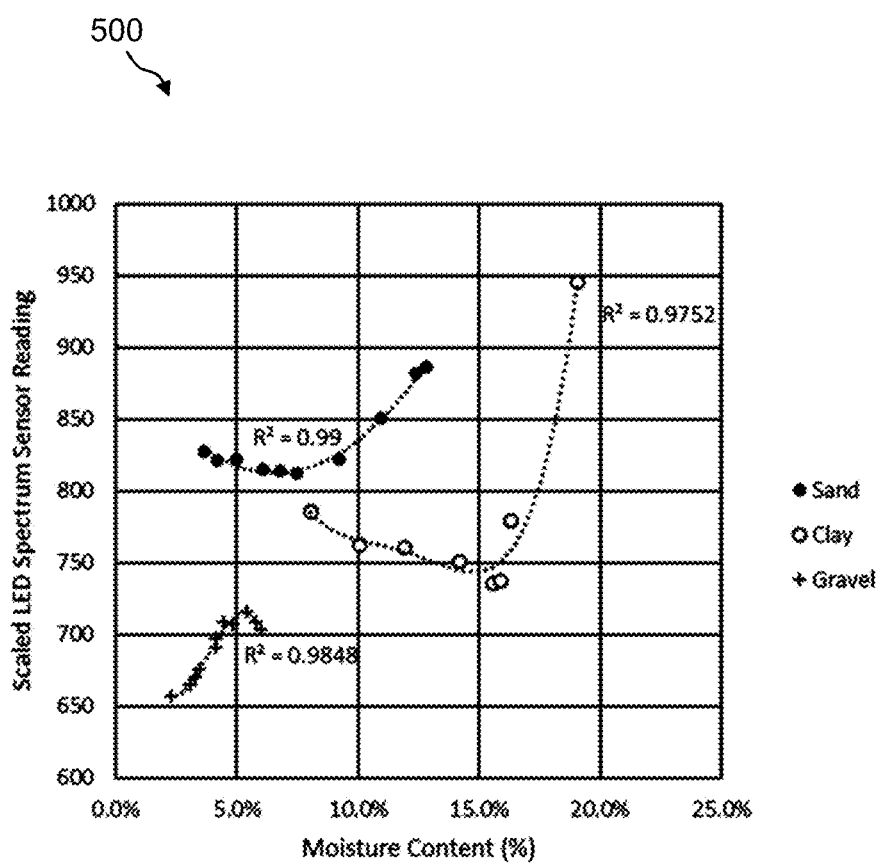
Figure 6:
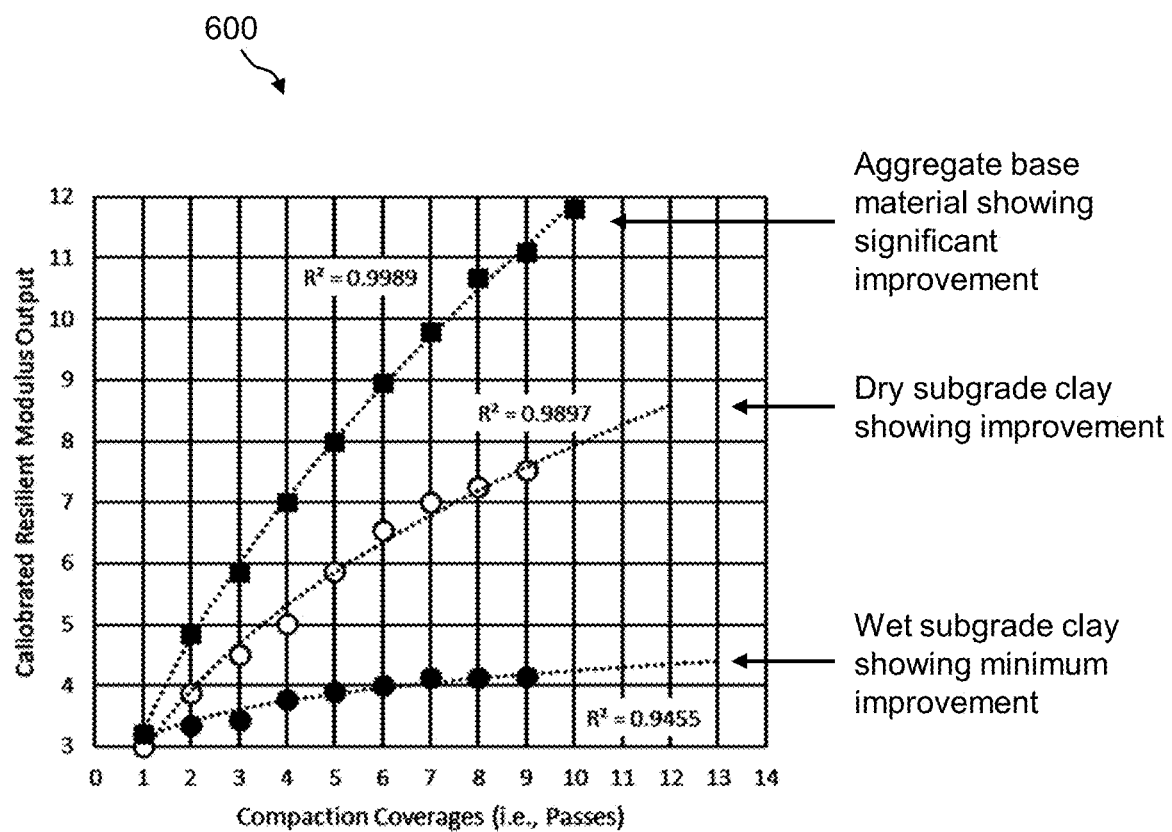
Figure 7:
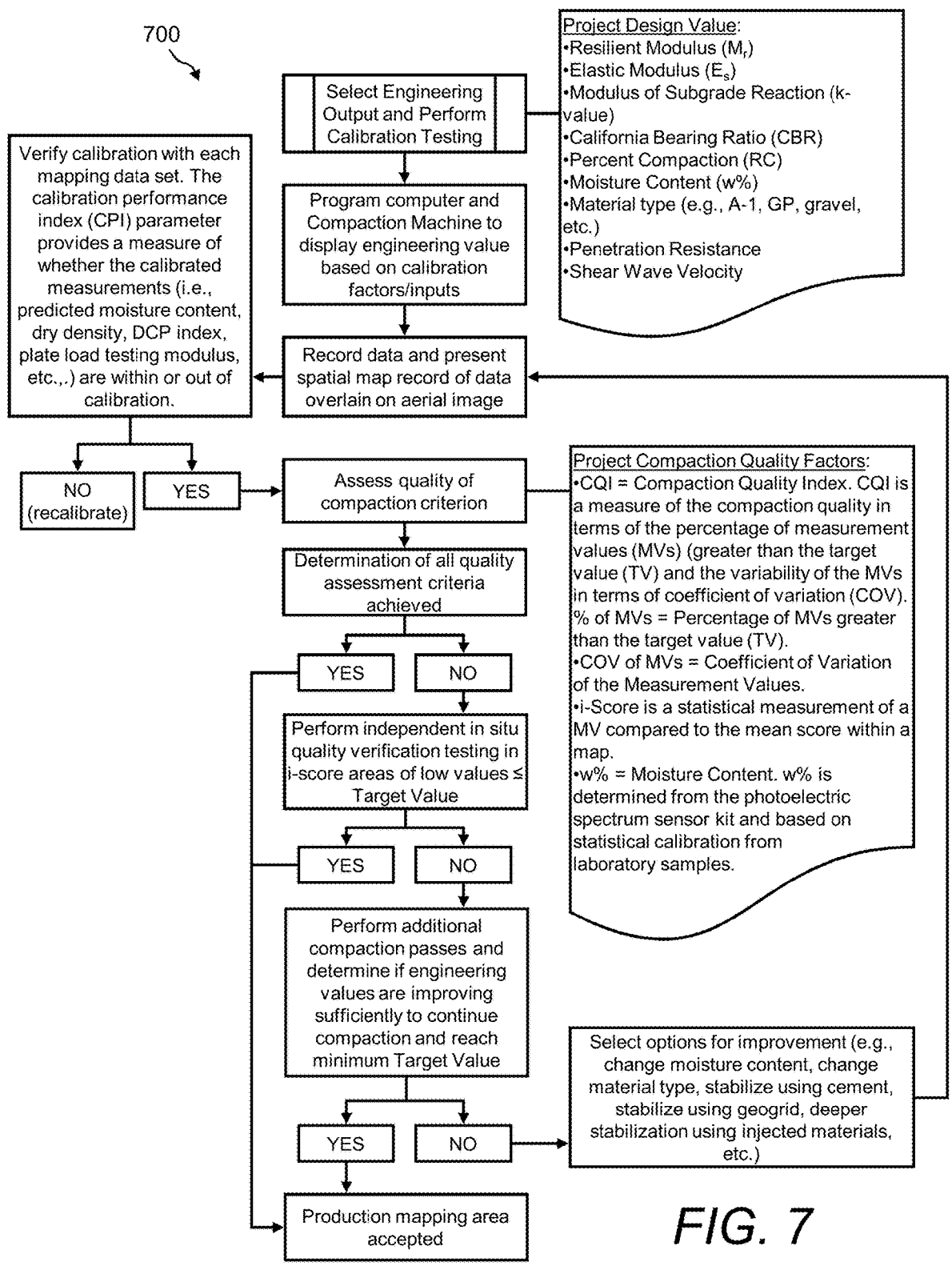
Figure 8:
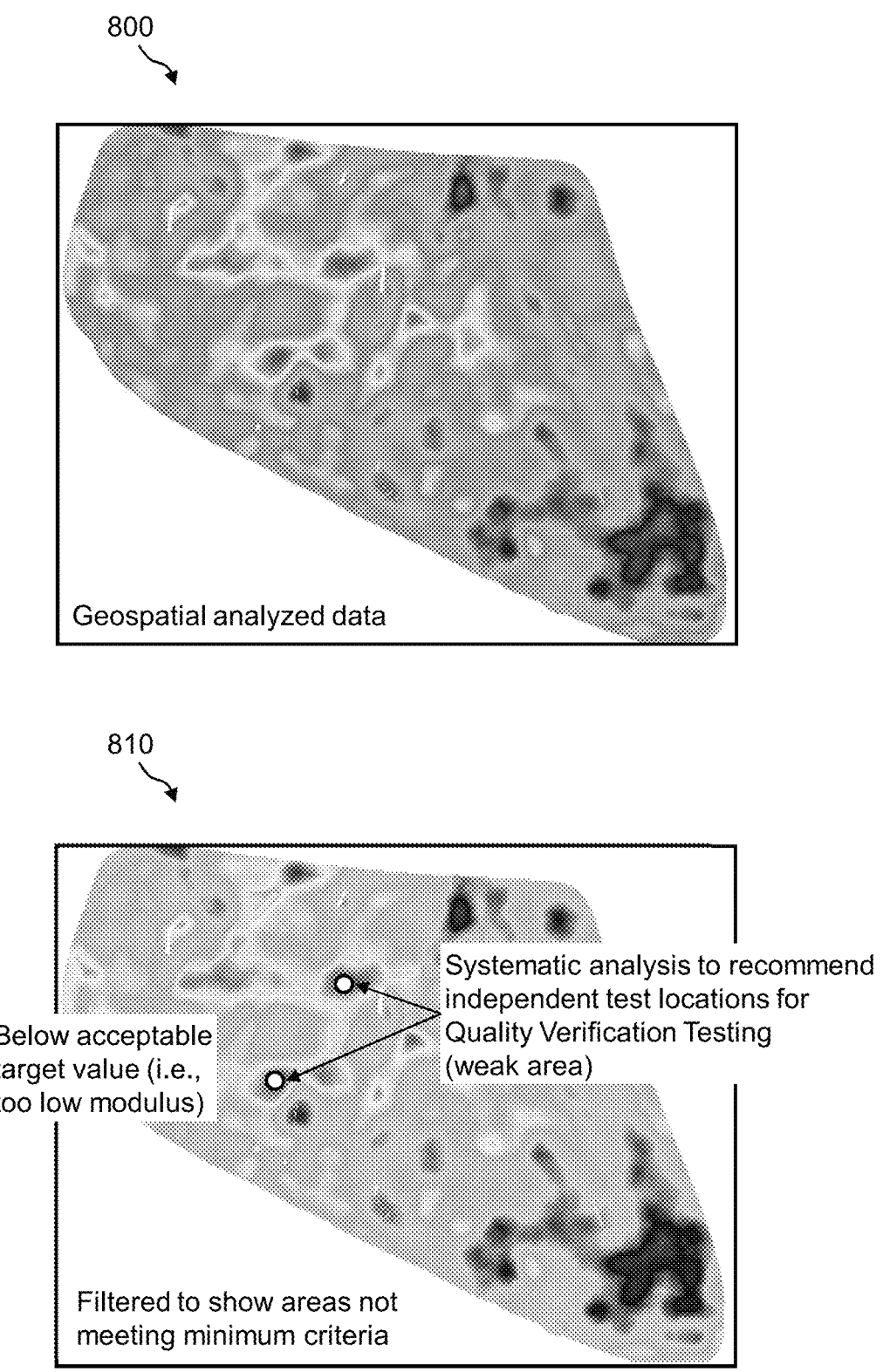
Figure 9:
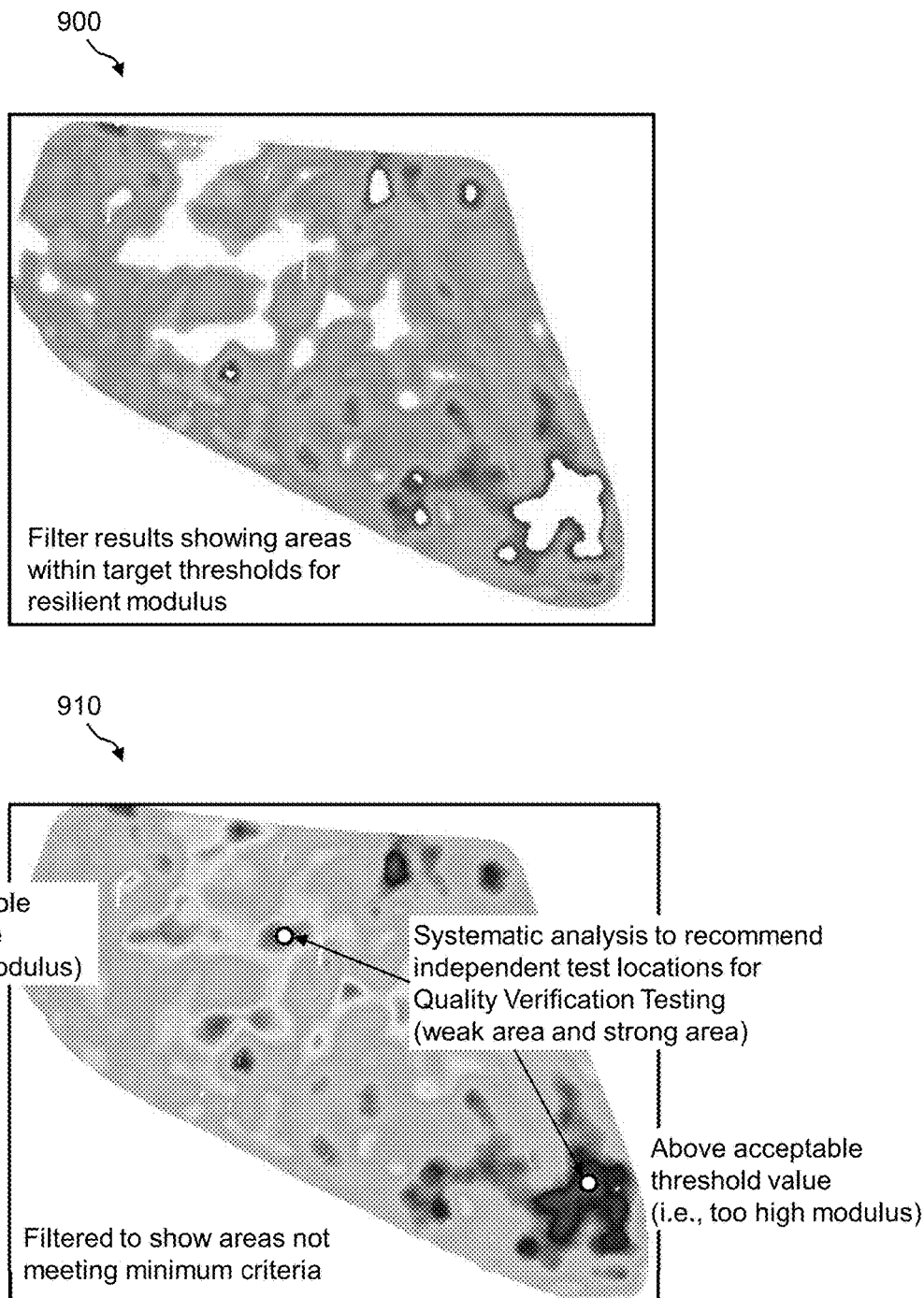
Figure 10:
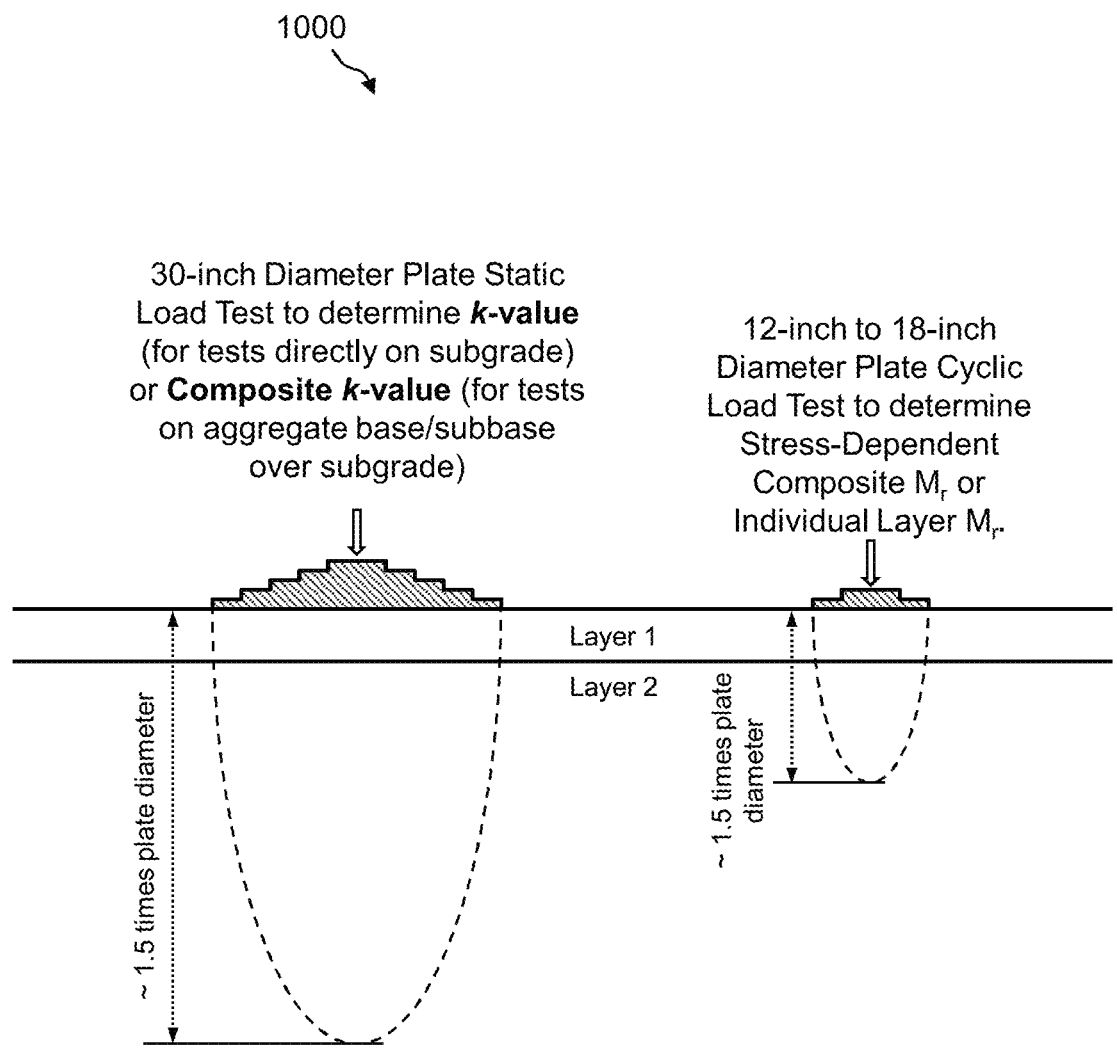
Figure 11:
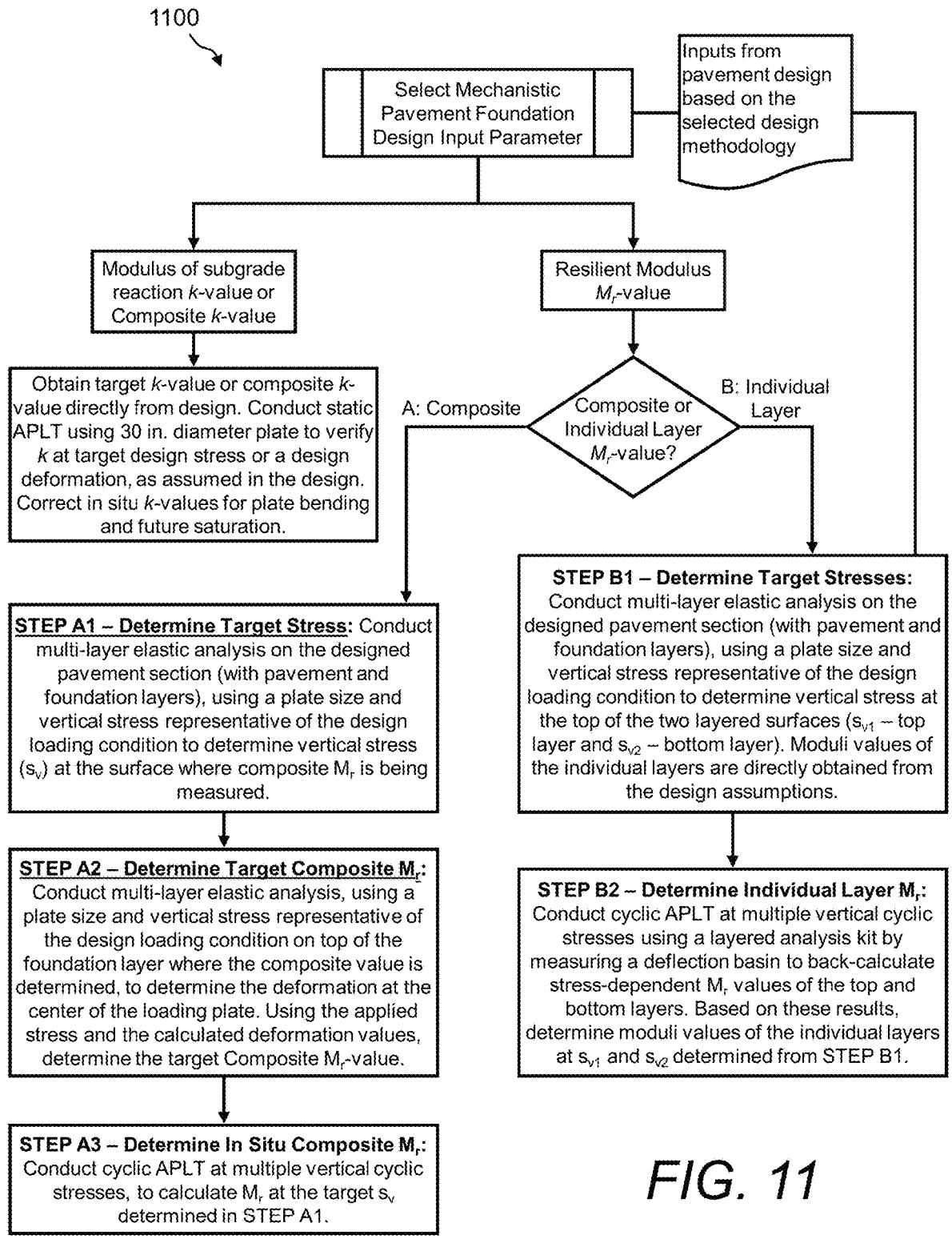

Having thus described the presently disclosed subject matter in general terms, reference will now be made to the accompanying drawings, which are not necessarily drawn to scale, and wherein:

FIG. 1 illustrates a side view of an example of the presently disclosed compaction control system for accurately determining properties of compacted and/or existing ground materials;

FIG. 2 illustrates a plot of an example of test point locations in a method of determining the spatial positioning in a calibration process of the presently disclosed compaction control system;

FIG. 3 and FIG. 4 illustrate various plots showing the calibrated engineering output of the presently disclosed compaction control system;

FIG. 5 illustrates a plot of an example of determining material type and moisture content for geo-materials using photo-electric sensors of the presently disclosed compaction control system;

FIG. 6 illustrates a plot of an example of changes in compaction improvement using the presently disclosed compaction control system;

FIG. 7 illustrates a flow diagram of an example of a method of assessing the improvement in compaction and then determining whether and/or when further ground improvement solutions are needed;

FIG. 8 and FIG. 9 show digital images of an example of the modulus results used to select locations for independent testing and spatial locations requiring ground improvement using the presently disclosed compaction control system;

FIG. 10 illustrates a schematic of zones of induced compressive stresses below loaded surface plates; and FIG. 11 illustrates a flow diagram of an example of a method of determining stiffness modulus values from multiple plate loading tests.

DETAILED DESCRIPTION

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a compaction control system for and methods of accurately determining properties of compacted and/ or existing ground materials. The presently disclosed compaction control system and methods provide integrated compactor measurements and control processes to verify design values and improve spatial uniformity of the ground. Namely, the compaction control system and methods provide measurement, analysis, design verification, and control of the spatial uniformity of engineering properties (e.g., modulus/stiffness, density, moisture content, material type, shear strength, compressibility, and layer thickness) for compacted materials and existing ground.

The presently disclosed compaction control system includes a specially-equipped and field-calibrated soil compaction machine, geo-spatial data analytic algorithms, and optimized process control actions to rapidly evaluate and control in situ modulus (elastic modulus, resilient modulus, modulus of subgrade reaction, and track modulus) and other engineering values. The compaction control system prescribes construction processes and measurement technologies to efficiently improve ground conditions. The presently disclosed compaction control system and methods can be used for engineered ground, pavement foundation systems and embankments, levees, railway track bed systems and embankments, landfills, and the like.

Referring now to FIG. 1 is a side view of an example of the presently disclosed compaction control system 100 for accurately determining properties of compacted and/or existing ground materials. Namely, the compaction control system 100 provides mechanisms to robustly determine compacted material properties, such as stiffness, in a spatially significant framework and provide real-time output and visualization of the properties to allow for real-time decision making regarding potential corrective actions to be taken at non-conforming locations. The compaction control system 100 provides a means to determine the material properties with high accuracy, thus facilitating the use of the system on actual construction projects. The compaction control system 100 further provides a means for determining soil moisture content and material consistency that are required to achieve adequate and appropriate quality control. The compaction control system 100 includes a mechanical compactor, such as, for example, a compaction machine 110. An arrangement of specially designing instruments is mounted on the compaction machine 110. Additionally, the compaction machine 110 includes a spatial positioning system, system calibration, and an integrated reporting and visualization system that can be used to make decisions in real time.

The compaction machine 110 is an example of heavy soil compaction equipment. Generally, such compaction machines can include smooth compaction rollers, such as static smooth compaction rollers and vibrating smooth compaction rollers. In the compaction control system 100, the compaction machine 110 includes a vibrating smooth compaction roller; namely, a vibratory drum 112. Vibratory drums, such as the vibratory drum 112, are made to vibrate by employing, for example, rotating or reciprocating mass.

The compaction machine 110 is equipped with sensors to determine position and heading, vibration amplitudes at selected frequencies, and material type and moisture content information. By way of example, FIG. 1 shows the placement of certain instrumentation on the compaction machine 110 and in relation to the vibratory drum 112. For example, the compaction machine 110 is equipped with location measurement system 120 and acceleration sensors 140 mounted on and/or near the vibratory drum 112. In one example, the location measurement system 120 is mounted atop the cab of the compaction machine 110.

The location measurement system 120 may include any device that can determine its geographical location to a certain degree of accuracy. For example, the location measurement system 120 may include a global positioning system (GPS) with an optional inertial measurement unit (IMU) 122, dual antennas, and/or Real Time Kinematic (RTK) satellite navigation signal corrections to provide spatial position, travel direction, travel speed, and elevation of the compaction machine 110. Namely, the location measurement system 120 may include a GPS receiver, such as a global navigation satellite system (GNSS) receiver. A GPS receiver may provide, for example, any standard format data stream, such as a National Marine Electronics Association (NMEA) data stream. The location measurement system 120 may also include an error correction component (not shown), which may be any mechanism for improving the accuracy of the geo-location data. In another embodiment, the location measurement system 120 may include any device or mechanism that may determine location by any other means, such as by performing triangulation (e.g., triangulation using cellular radiotelephone towers). An offset value is known of the physical location of the location measurement system 120 with respect to the center of the vibratory drum 112 (the compaction roller) at the ground elevation. Accordingly, using the location measurement system 120, position information is provided for the center of the vibratory drum 112 at the ground elevation.

An inertial measurement unit, such as the IMU 122, is an electronic device that measures and reports an object's acceleration, orientation, and gravitational forces by use of one or more inertial sensors, such as one or more accelerometers, gyroscopes, and compasses. The IMU 122 may be any commercially available IMU device for reporting the acceleration, orientation, and gravitational forces of any device in which it is installed. In one example, the IMU 122 may be the IMU 6 Degrees of Freedom (6 DOF) device available from SparkFun Electronics (Niwot, Colo.). This SparkFun IMU 6 DOF device has Bluetooth® capability and provides 3 axes of acceleration data, 3 axes of gyroscopic data, and 3 axes of magnetic data. IMU data from IMU 122 is an example of information that may be used in the processes of the compaction control system 100.

The compaction machine 110 is also equipped with a specially designed accelerometer sensor 140 that outputs vibration (one dimensional (vertical) or three-dimensional (i.e., x, y, z)) amplitude for a pre-determined amplitude range at selected multiples and partial multiples of the harmonic and sub-harmonic frequencies (e.g., 1/2, 1, 2, 3/2, 5/2, 3, 7/2, and 9/2 times the fundamental vibration frequency). To provide for suitable accuracy and calibration, the accelerometer range is specifically selected to provide maximum peak amplitude outputs at the multiples and partial multiples of the harmonic and sub-harmonic frequencies while (a) not exceeding the amplitude range at the fundamental (vibration) frequency and (b) providing a stable sensitivity response up to about 200 Hz. We have determined that the accelerometer range for soft clays, stiff clays, stabilized subgrade, aggregate base, and stabilized aggregate base materials are 5 g, 10 g, 25 g, 25 g, and 50 g. Acceleration sensors that are sensitive to these ranges are selected for measurements.

An accelerometer is a device for measuring acceleration and gravity-induced reaction forces. A multi-axis accelerometer is able to detect magnitude and direction of the acceleration as a vector quantity. The acceleration specification may be in terms of g-force, which is a measurement of an object's acceleration. Accelerometer data from the accelerometer sensor 140 is an example of information that may be used in the processes of the compaction control system 100.

Optionally, the compaction machine 110 is equipped with a full-spectrum photoelectric sensor 130, which is a visual measurement sensor. In one embodiment, the full-spectrum photoelectric sensor 130 is a full-spectrum white light-emitting diode (LED) sensor. Unlike other imaging or digital imaging methods, the photoelectric sensor uses a detector that measures the full color spectrum. The sensor uses a powerful white light source to enable detection of small difference in color especially for the darker spectrum of colors associated with soil and earth materials. The sensor outputs are provided as an analog output that optionally depends on (a) both color and intensity (degree of reflection), (b) color separately, and (c) intensity separately. By calibrating the sensor output to the specific materials encountered at a project site, the full-spectrum photoelectric sensor (130) predicts soil moisture content with a high degree of accuracy.

The full-spectrum photoelectric sensor 130 has a field of view (FoV) 132. For example, the full-spectrum photoelectric sensor 130 is affixed to the underside of compaction machine 110 with its FoV 132 facing downward toward the ground. The full-spectrum photoelectric sensor 130 may have a vertical offset distance of, for example, from about 1 inch to about 40 inches from ground elevation and a focus area diameter of, for example, from about 1 inch to about 4 inches at the ground elevation. The FoV may be angled to be orthogonal to the compacted surface or oblique to the compacted surface. Measurements in both orthogonal and oblique directions may be compared and used simultaneously to provide for correlations to soil moisture content and consistency. In the compaction control system 100, the full-spectrum photoelectric sensor 130 can be used to distinguish between different material types (e.g., gravel, clay, etc.) and/or variations in moisture content that change color for a given material.

Referring still to FIG. 1, a controller 150 with a corresponding display 160 may be provided in the cab of the compaction machine 110. The controller 150 can be any standard controller or microprocessor that is capable of processing program instructions. The controller 150 serves to provide processing capabilities, such as storing, interpreting, and/or executing software instructions, as well as controlling the overall operations of the compaction control system 100. The display 160 can be, for example, any standard LED touchscreen display that is suitably sized for this application. The display 160 may be conveniently positioned in the cab of the compaction machine 110 for easy use and viewing by the user. The controller 150 and the display 160 can be separate or integrated together. For example, the controller 150 and the display 160 can be a tablet device or smartphone such as those available from Apple, Microsoft, Amazon, Samsung, and Google.

The controller 150 is in communication with any and all instrumentation installed on the compaction machine 110. For example, the controller 150 may be connected in wired and/or wireless fashion with the location measurement system 120, the full-spectrum photoelectric sensor 130, and the accelerometer sensor 140. Certain software may be installed and running on the controller 150 for executing the processes of the compaction control system 100. In one example, certain geo-spatial data analytic algorithms 152 are running on the controller 150 whereby information from the location measurement system 120, the full-spectrum photoelectric sensor 130, and/or the accelerometer sensor 140 is processed and then spatial color-coded data overlain on a georeferenced aerial image can be displayed.

The accelerometer sensor 140 is positioned on the center axis of the vibratory drum 112 to measure the drum vibration and the full-spectrum photoelectric sensor 130 is placed behind the vibratory drum 112. The location measurement system 120, the full-spectrum photoelectric sensor 130, and the accelerometer sensor 140 are used to provide spatially indexed, but uncalibrated, values of relevant compaction material properties to the controller 150. Examples of relevant compaction material properties may include, but are not limited to, resilient modulus ($M_r$), elastic modulus ($E_s$), modulus of subgrade reaction (k), California Bearing Ration (CBR), percent relative compaction (RC), moisture content (w), material classification, penetration resistance, shear wave velocity, and the like.

The accelerometer sensor 140 is selected to provide outputs in the range of from about 0.005 g to about 50 g of the maximum acceleration values produced by the compaction machine 110. During compaction at a given location, the measured amplitude values are analyzed using Discrete Fourier Transformation (DFT) or Fast Fourier Transformation (FFT) analyses to provide measurements at selected fundamental (frequencies). Output values are also analyzed for harmonic frequencies corresponding to 1, 1/2, 3/2, 5/2, 7/2, 9/2, 2, 3, 4 and 5 times the fundamental frequency. Following the amplitude measurement and the determination of harmonic responses, the following process is used to provide a robust matrix of interactive correlation values:

(1) Normalize all response parameter values by the amplitude the fundamental frequency "A", for example: 2A/A, 1/2A/A, 3/2A/A, 5/2A/A, 7/2A/A, 9/2A/A, 2A/2, 3A/A, 4A/A, and 5A/A; where "2A", "1/2A", "5/2A" etc. denote the amplitude values measured at 2, ½, and 5/2 times the fundamental frequency;

(2) Normalize all response parameter by "1/2A+A", for example: 2A/(1/2A+A), 3/2A/(1/2A+A), . . . ; where "1/2A+A" denotes the amplitude values measured at 1.5 times the fundamental frequency, and where "2A", "3/2A", etc. denote the amplitude values measured at 2, and 1.5 times the fundamental frequency;

(3) Square the response parameter values, for example: $A^2$, $3/2A^2$ . . . ; where "A" and "3/2A" denote the amplitude values measured at 1 and 3/2 times the fundamental frequency; and (4) Cross multiple parameters, for example: 3/2A×5/2A; where "3/2A" and "5/2A" denote the amplitude values measured at 1.5 and 2.5 times the fundamental frequency.

Referring now to FIG. 2 is a plot 200 of an example of test point locations in a method of determining the spatial positioning in a calibration process of the presently disclosed compaction control system 100. As shown in FIG. 2, the compaction control system 100 is used to provide a calibration pass the site. The results of the acceleration measurements are plotted vs spatial position to indicate the discrete stiffness values at each location and to determine the optimal calibration locations.

The compaction control system 100 can be used for the calibration of material properties referenced above. In this embodiment, the vibration outputs of accelerometer sensor 140 at the vibratory drum 112 provide, for example, machine speed, pitch, and roll to elastic modulus, resilient modulus, shear modulus, modulus of subgrade reaction, or other stiffness or design strength engineering parameter values. These the vibration outputs and/or values are calibrated using a carefully designed algorithm (e.g., geo-spatial data analytic algorithms 152) to provide high accuracy.

The plot 200 depicts a method of determining the spatial positioning of the calibration process. The accelerometer "response" parameters and the various interaction parameters described above are correlated to independent measurements, such as automated plate load tests, conducted at the spatial locations in which the dynamic measurements are made. The minimum sample size needed for this calibration effort is determined using a procedure recommended by Dupont and Plummer (1998). The location of the calibration test is based on detailed geospatial analysis of the initial mapping pass, whereby the geospatial analysis processes the results using a cluster analysis process. The identification of calibration points using Geospatial analysis involves several analysis steps to statistically identify clusters of points with high values and clusters of points with low values. After projecting the data to a grid of points (spaced horizontally 1 ft×1 ft on-center), the data is processed to identify aggregated points that are in proximity to one another based on a set distance. Accelerometer output values, denoted as "XMV" values, with similar high values or low values to define a cluster. The data is processed to return a statistical "z-score", and when analyzing the grid points together, the outputted z-score will indicate if clustering is found in the data or not. To provide a high-quality calibration analysis, we learned that testing only at point of high values or low values does not deliver the desired high regression coefficient ($r^2 > 0.9$). It was determined that although there may be an XMV value with a high value, it may not be a statistically significant area. In order to be a significant calibration test location, an XMV values with a high value must be surrounded by other XMV high values. The Geospatial analysis determines the locations of clusters of similarly high or low XMV values that are then used to determine calibration locations. Independent calibration tests at these "high" and "low" value cluster locations produce the most robust calibrations (coverage form high values to low values) and the most statistically significant results.

Calibration is typically achieved with approximately 5 to 30 test point measurements. Calibration is achieved by comparing the various sensor outputs and machine parameters to the independently measured calibration values, such as those that may be obtained with automated plate load tests described in U.S. Pat. No. 9,395,287.

Other methods may also be used to achieve calibration, including: falling weight deflectometers, lightweight deflectometer measurements, dynamic cone penetrometer measurements, static cone penetrometer measurements, Standard Penetration Test measurements, pressure meter measurements, dilatometer measurements, and so on.

The plot 200 of FIG. 2 shows an example of the selection of calibration test locations for plate load testing (or other independent engineering or compaction measurements) with the solid line showing measured variation from one of the vibration amplitude parameters and selected calibration testing points that cover the range of sensor outputs ranging from the lowest to highest values. Calibration analysis is comprised of multivariate statistical regression between the sensor outputs (independent variables: position, speed, pitch, roll, vibration amplitudes at selected frequencies, and/or white LED spectrum outputs including average values and changes in values/variation) and the independent field measured soil mechanical properties (dependent variables such as stress-dependent resilient modulus values from automated plate load testing, penetration resistance with depth from dynamic cone penetrometer, modulus of subgrade reaction values from plate load testing including a range of plate diameters to account for different measurement influence depths, California bearing ratio values, and shear wave velocity).

The multiple regressions are performed for calibration using either a stepwise regression method or a backward elimination method. The backward elimination method starts with including all possible independent variables at one time and then methodically eliminating variables that do not have high statistical significance (i.e., statistical probability, $p<0.05$) in the multivariate model. The stepwise regression method works in the other direction starting with adding one independent variable at a time to the model. Both processes are continued until the highest correlation coefficient ($R^2$) and the lowest standard error for prediction are achieved.

Referring now to FIG. 3 and FIG. 4 that present various plots showing the calibrated engineering output of the presently disclosed compaction control system 100. Namely, FIG. 3 shows a plot 300 of the calibrated sensor outputs to composite resilient modulus for one homogeneous layer. FIG. 3 shows a plot 400 and a plot 410 of the results of the calibration method applied to a layered deposit. That is, the plot 400 (layer 1) and the plot 410 (layer 2) show plots of the calibrated sensor outputs to layered resilient modulus values.

The plot 300 of FIG. 3 shows an example of predicted versus measured results modulus for sandy clay fill material. Unlike the results achieve by most geotechnical correlations, the regression results performed at nine project sites have surprisingly shown very high-quality correlations corresponding to $R^2$ values consistently greater than 0.9. These values are almost twice the relatively highly variable $R^2$ values of approximately 0.5 or less that are reported for traditional compaction methods.

Again, the plot 400 (layer 1) and the plot 410 (layer 2) of FIG. 4 show the results of the calibration method applied to a layered deposit. Calibration is performed for the ground conditions assuming homogenous conditions (i.e., composite values) or using layered analysis by accounting for different engineering properties (e.g., aggregate base versus underlying subgrade resilient modulus values) for defined layers and layer thicknesses. Layered engineering properties are determined by performing in situ tests at selected elevations within the ground profile, using a combination of different plate load test diameters (e.g., 6-inch to 30-inch diameter, as shown in FIG. 10. at the top of a layered profile, and plate load testing with deflection basin measurements (deflection of the ground away from the edge of the loading plate) and performing elastic layered analysis (back-calculation). FIG. 4 shows an example of calibration results for a layered profile of 12-inch thick aggregate base over clay subgrade. Regression analysis and the associated calibration factors allow for real-time calculations of modulus values for both layers during compaction. This is particularly valuable information for pavement foundation design verification where each layer may have minimum modulus requirements. This information may also be used with control processes during compaction to determine if low modulus areas are attributed to the upper layer or attributed to a deeper lower layer. Unique to the layered analysis is that the vibration response for the composite system (hard layer over soft layer, or soft layer over hard layer) provides a unique frequency-amplitude response that is independent of the composite modulus. By calibrating the vibration response to the in-situ modulus for each layer, the amplitudes and harmonics that are statistically significant are determined.

FIG. 5 illustrates the determination of material type and moisture content for geo-materials using photo-electric sensors of the presently disclosed compaction control system 100. The plot 500 shows the relationship between moisture content and spectrum sensor readings for three different material types: clay, sand, and aggregate at a project site. Because the calibration factors and models are often material dependent, material type determined from the white photo-electric spectrum sensor shows when changes in material type occur. The data shown in FIG. 5 indicate that the sand material exhibits spectrum sensor readings of greater than 800; the clay material exhibits readings generally ranging between 730 and 800; and the aggregate material exhibits readings less than 720. Thus, a given sensor reading indicates both the material type and moisture content of the material. For example, a reading of 750 indicates clay material with a moisture content value of 14%.

The material sensor is used to document that the correct materials are placed at the correct location within a fill layer. The photo-electric output includes intensity for a selected focal distance (32 inches from surface for a selected focal diameter (1-inch circle) at the surface of the tested material. The white LED spectrum sensor output is also calibrated using regression analysis to determine the moisture content of a given material.

The plot 500 shows an example of three dissimilar materials with each material tested for a range of moisture contents (independently measured using the oven drying method). The "response" output is correlated to independent measurement including: (1) soil classification, (2) soil color, (3) soil texture, (4) soil moisture content at surface and at 6 or 12 inches below the surface.

Once the calibration results are analyzed, calibration factors are utilized within the algorithms on the controller 150 to determine site- and calibration-specific stiffness and resilient modulus values for material-specific and site-specific conditions. Calibration validity is then monitored using the calibration performance index (CPI) parameter that provides an assessment of whether the calibrated measurements (i.e., predicted moisture content, dry density, DCP index, plate load testing modulus, etc.) are within or out of calibration. The CPI parameter value is determined for each compaction map area, using the calibration test results in comparison to a ratio of the upper and lower limits of calibration relative to the average and standard deviation of the measured data. The importance of this analysis is that it provides an alert to the engineer and operator when the ground conditions are outside of the initial calibration limits, which then can trigger additional calibration testing.

Following calibration and inputting calibration factors into the analysis computer program on the controller 150 of the compaction machine 110, the compaction information is presented (via the display 160) to the operator in real-time showing the spatial location and selected engineering measurement values of the ground that are color-coded based on an established color scale. The color-coded spatial record identifies the position of the measurement, the scaled engineering value, the material type (e.g., subgrade, aggregate base, clay, sand, gravel, etc.), predicted moisture content of a given material type (e.g., 5% to 23%). This information is used to determine areas that do not meet the minimum or threshold engineering parameter value requirements established for site and materials. For areas with multiple roller coverages (i.e., roller passes), the record of roller coverages versus selected engineering values can be used to show trends in engineering measurement value changes as a function of roller passes. This is particularly useful to monitor in regions of the evaluation area that are below the minimum design value or outside target thresholds.

Referring now to FIG. 6 is a plot 600 of an example of changes in compaction improvement using the presently disclosed compaction control system 100. For example, the plot 600 shows an example of modulus compaction curves for wet subgrade, dry subgrade, and aggregate base. Namely, the bottom curve shows slight improvement in compaction with increasing roller passes for a clay material due to wet conditions, the middle curve show moderate compaction improvement for the same clay material but in a comparatively lower moisture content, and the upper curve shows significant compaction improvement (resilient modulus) for an aggregate base material. For material and moisture conditions that do not show improvement with additional roller passes, the operator needs to change the construction process are implement a ground improvement process.

To supplement the visual color-coded results, a georeferenced aerial image may be used as a background to the geospatial data overlay. The aerial image provides the engineer and operator a connection between the results and a visual record of the aerial photo ground conditions. The aerial photo selected from selected past dates can show materials or other structures such as building, pavements, and vegetation. Recent aerial images such as captured from a georeferenced drone show conditions very near to the time of collecting the compaction data. The aerial image information is used to assist with identifying why the calibrated engineering outputs vary spatially such as in areas that required fill (low modulus values) and buried pavements (high stiffness values).

Records of the calibrated outputs for engineering parameters, material type, and moisture content coupled with aerial images and machine pass coverages establish a basis to predict compaction response and recommend construction process control changes and/or changes in materials type, moisture content, and various ground improvements solutions such as chemical stabilization and mechanical stabilization.

FIG. 7 illustrates a flow diagram of an example of a method 700 of assessing the improvement in compaction and then determining whether and/or when further ground improvement solutions are needed. For example, the method 700 shows how the analyzed data can be used to prescribe future construction process and/or material improvements and/or stabilization.

Using the method 700, the prescribed improvements can be derived from past calibration records with similar conditions or from constructing test beds and calibrating the results as described previously. The benefit of prescribing construction process control and improvements is to make the construction process more efficient and to ensure that the desired engineering requirements for a project are met. Typically, the primary actuation to improve compaction and engineering properties of ground is the compaction. Analysis of the results presented in the plot 600 shown in FIG. 6 can be analysis using regression analysis to develop a predictive model that shows the level of improvement offered for future compaction passes. In some situation the models show that improvement to engineering values (modulus) can be obtained economically with additional roller passes, however achieving the desired modulus is often not possible especially in weak or wet underlying ground conditions. When these situations are analyzed, prescribed improvements in lieu of compaction can be established involving over excavation and replacement of the weak material with stronger materials, chemical stabilization (e.g., mixing cement into the existing materials), moisture conditioning (i.e., reduce by aeration or adding water to the ground), shallow ground improvements (e.g., small diameter aggregate columns), use of geogrid or other mechanical reinforcement products.

FIG. 8 and FIG. 9 show digital images of an example of the modulus results used to select locations for independent testing and spatial locations requiring ground improvement using the presently disclosed compaction control system 100.

For example, an image 800 of FIG. 8 shows an example of a spatial modulus compaction map results for compacted silt. Then, an image 810 of FIG. 8 shows an example of isolating spatial areas showing the dependence that do not meet the minimum design requirements. Additionally, an image 900 of FIG. 9 shows an example of a spatial modulus compaction map excluding values outside of maximum and minimum design threshold modulus values. Then, an image 910 of FIG. 9 shows an example of isolating spatial areas showing the dependence that fall outside the minimum and maximum design requirements.

FIG. 8 and FIG. 9 show an example data set using spatial analysis to determine areas require improvement and recommended independent in situ testing locations.

The compaction spatial maps can also establish systematic independent quality control test locations. Typically, quality control testing location are selected randomly. Using the described systematic sampling locations based on the spatial engineering parameter maps (e.g., resilient modulus), the benefits include evaluating conditions at locations that are either too stiff or too soft and reduction in discrete point testing frequency.

The maps shown in FIG. 8 and FIG. 9 may also be configured to show surface elevation at the end of each compaction pass. By knowing the surface elevations of two successive compaction operations conducted on two successively placed fill layers, maps of layer thickness may be easily created and viewed for quality control purposes. These maps may, along with maps of layer stiffness, form the basis of "as built" construction documents.

EXAMPLES

Example 1

The present subject matter was deployed at a project site under the control of a design-build contractor in central Illinois. The site consisted of the construction of eight lane-miles of new interstate highway by a design-build contractor that was motivated to achieve demonstrated quality (density) of the compacted materials because future repairs to the highway would be incurred by the design-build team over time after the completion of construction. The contractor elected to compact the granular sub-base and base course materials with a smooth drum vibratory roller capable of imparting a maximum acceleration value of about 2 g during compaction. The compactor was equipped with a three-axis accelerometer having a maximum amplitude of about 25 g. The accelerometer amplitude values were selected to provide output values of from about 0.005 g to about 5 g based on the maximum imparted acceleration values of the machine. This was so that the accelerometers could provide sufficient accuracy during calibration. The compaction machine was further equipped with a high accuracy GPS device capable of providing 3-D positioning measurement with about a 0.2 m accuracy. The machine was further equipped with a photo-electric sensor suitable to measure the color and intensity of the compacted materials.

After mounting the accelerometers on the compaction machine, a trial pass was performed while spatially determining acceleration values during compaction. The acceleration amplitudes were analyzed using Fast Fourier Transformations (FFT) at selected frequencies (sub-harmonic and multiples of harmonics). The FFT analyses generated "response" parameter values including amplitude values at fundamental vibration frequencies of 1, ½, 3/2, 5/2, 7/2, 9/2, 2, 4, and 5 times the fundamental (natural) frequency. The following process was used:

(1) Normalize all response parameter to A: 2A/A, 1/2A/A, 3/2A/A, 5/2A/A, 7/2A/A, 9/2A/A, 2A/2, 3A/A, 4A/A, and 5A/A;
(2) Normalize all response parameter to 1/2A+A: 2A/(1/2A+A), 3/2A/(1/2A+A), . . . ;
(3) Square response parameters, e.g., $A^2$, $3/2A^2$, . . . ; and
(4) Cross multiple parameters, e.g., $3/2A \times 5/2A$ A variety of in-situ tests were then performed at the site to provide baseline verification measurement values. These tests included Automated Plate Load Tests such as those described in U.S. Pat. No. 9,395,287 conducted at multiple locations to determine the composite resilient modulus, layered resilient modulus, and permanent deformation values. Alternatively, measurements comprised of falling weight deflectometer tests, lightweight deflectometer tests, penetration dynamic cone penetration resistance tests, static cone penetration test resistance tests, Standard Penetration Resistance tests, pressure meter tests, dilatometer tests, or other tests used to determine stiffness modulus values could have each been used to form the baseline calibration values.

The accelerometer "response" parameter values and the APLT-generated baseline resilient modulus values were then correlated using multiple regression analyses. The minimum sample size needed for this calibration effort is determined using a procedure recommended by Dupont and Plummer (1998). The regress analysis results demonstrate statistical regression parameter with high-quality correlations, $R^2 \geq 0.9$ and low standard error values. Surprisingly, these results were significantly higher than those previously determined (Refs) by the prior art methods, which provide $R^2$ values often less than 0.5. The significantly high $R^2$ values of greater than 0.9 provided confidence needed by the constructors to continue to employ the Invention in the construction operations.

Example 2

At a project site consisting of new asphalt pavement in Minnesota, the following regression analysis procedure was used to for the compaction modulus correlations. The correlation analysis was performed using multi-variate statistical regression procedure involving two primary steps: (1) assessing directionality and correlation between each independent variable and the predicted variable and selecting the variables to include in the model, and (2) estimating the model by using the backward selection based statistical regression method of entry.

In the first step, the directionality (whether +ve or −ve and whether data transformation was needed to make relationships linear) and the correlations between each independent predictor variable and the predicted variable were assessed using individual scatter plots. All independent variables that show statistically significant trends at a probability level of 95% or above (p=0.05) were selected for the initial regression modeling in step 2. The number of variables selected were also be based on the number of test measurements available for regression analysis. In general, at least 2 to 3 data points are required per independent variable.

In the second step, the backward selection based statistical regression method of entry into the model was followed. This method involved first creating a model with all the selected variables (from step 1) into a multivariate linear regression model. Then, one predictor variable at a time was deleted to assess how it contributed to the overall variance of the estimate. The elimination process began with selecting the parameter with the highest p-value (which represents the least probability). The primary goal in the backward selected process was to reduce the number of independent variables in the model to only those that are necessary to account for the variance as accounted by included all the selected variables. The process stopped when all p-values of the predictor variables were less than the critical probability level (i.e., 0.05). Throughout the process, collinearity, caused by multiple predictor variables that are strongly related in the model, were reviewed by calculating the variance inflation factors (VIFs). The VIFs were kept as minimum as possible.

The strength of the regression model was assessed using the adjusted coefficient of determination ($R^2$ Adj.) value and the standard error of the estimate. Higher the $R^2$ Adj. value and the lower the standard error of the estimate, the stronger the correlation.

Example 3

An embodiment of the present subject matter was deployed at the test site in Minnesota wherein a new pavement system was being constructed for evaluation. During compaction, the compacted materials at different locations exhibited visibly different moisture contents. One area of the site was visibly dry and another was visibly wet. A digital image of the materials at the site was taken for spectral analysis and it was discovered that the spectral analysis correlated well with soil moisture content and material consistency. Further observations showed that the intensity of ambient light affected the correlations but that the LED spectrum provided consistent correlations.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. An apparatus for providing validated intelligent compaction measurements comprising:
   a. a roller compaction machine having a compaction machine drum used to apply dynamic compaction pressure to compacted materials;
   b. accelerometers used to measure the dynamic responses of the compacted materials;
   c. a positioning device used to determine the x-y-z position of the compaction machine drum;
   d. a first algorithm used to determine the real-time dynamic responses (vibration amplitudes at selected sub-harmonic and harmonic frequencies) of the compaction machine drum during compaction;
   e. a calibration tool used to calibrate the dynamic response values to independently measured in situ modulus and deformation at selected locations representing clustered regions ranging from the highest to lowest stiffness modulus locations;
   f. an output device used to identify x-y-z positions for locations of the compacted materials corresponding to the range of highest to lowest stiffness values; and
   g. a second algorithm used to provide validated site-specific stiffness modulus values for the site during compaction.

2. The apparatus of claim 1, further comprising acceleration sensors selected to provide maximum peak amplitude outputs at the multiples and partial multiples of the harmonic and sub-harmonic frequencies while (a) not exceeding the amplitude range at the fundamental (vibration) frequency and (b) providing a stable sensitivity response up to about 200 Hz.

3. The apparatus of claim 1, further comprising a photoelectric sensor device used to determine soil moisture content values and soil material type at the x-y-z positions measured during compaction operations.

4. The apparatus of claim 1, further comprising a visualization output to provide the operator with a real-time measurement of one or more of the following:
   a. compacted material stiffness values;
   b. material type;
   c. moisture content; and
   d. layer thickness.

5. The apparatus of claim 1, further comprising a calibration tool including a penetrometer to measure penetration resistance values at discrete locations.

6. The apparatus of claim 1, further comprising a calibration tool including an automated plate load test device used to determine the static or dynamic deformation and stiffness values of the compacted materials at discrete locations.

7. The apparatus of claim 6, wherein the automated plate load test device is performed with or without the addition of confining rings.

8. The apparatus of claim 1, wherein the second algorithm includes performing multiple linear regression analysis between compactor dynamic responses and independent composite (assumption of homogeneous ground) measurements.

9. The apparatus of claim 8, wherein the multiple linear regression analyses are performed using the multiple linear regression analysis between compactor dynamic responses and independent layered (determination of layered modulus and thickness values) measurements.

10. The apparatus of claim 1, further comprising a third algorithm added to determine if the measured compaction stiffness values are in conformance with the project specifications.

11. The apparatus of claim 10, further comprising a fourth algorithm added to determine if the measured material type values are in conformance with the project specifications.

12. The apparatus of claim 11, further comprising a fifth algorithm added to determine if the measured moisture content values are in conformance with the project specifications.

13. The apparatus of claim 1, further comprising a sixth algorithm added to determine the future number of construction passes required to achieve the system requirements.

14. The apparatus of claim 10, wherein the conformance is provided using a visualized output to the compaction machine operator.

15. An apparatus for providing validated intelligent compaction measurements comprising:
   a. a roller compaction machine having a compaction machine drum used to apply dynamic compaction pressure to compacted materials;
   b. accelerometers used to measure the dynamic responses of the compacted materials;
   c. a positioning device used to determine the x-y-z position of the compaction machine drum;

d. a first algorithm used to determine the real-time dynamic responses (vibration amplitudes at selected sub-harmonic and harmonic frequencies) of the compaction machine drum during compaction;
e. a calibration tool used to calibrate the dynamic response values to independently measured in situ modulus and deformation at selected locations representing clustered regions ranging from the highest to lowest stiffness modulus locations;
f. an output device used to identify x-y-z positions for locations of the compacted materials corresponding to the range of highest to lowest stiffness values;
g. a second algorithm used to provide validated site-specific stiffness modulus values for the site during compaction; and
h. a photoelectric sensor device used to determine soil moisture content values at the x-y-z positions measured during compaction operations.

16. An apparatus for providing validated intelligent compaction measurements comprising:
a. a roller compaction machine having a compaction machine drum used to apply dynamic compaction pressure to compacted materials;
b. accelerometers used to measure the dynamic responses of the compacted materials;
c. a positioning device used to determine the x-y-z position of the compaction machine drum;
d. a first algorithm used to determine the real-time dynamic responses (vibration amplitudes at selected sub-harmonic and harmonic frequencies) of the compaction machine drum during compaction;
e. a calibration tool used to calibrate the dynamic response values to independently measured in situ modulus and deformation at selected locations representing clustered regions ranging from the highest to lowest stiffness modulus locations;
f. an output device used to identify x-y-z positions for locations of the compacted materials corresponding to the range of highest to lowest stiffness values;
g. a second algorithm used to provide validated site-specific stiffness modulus values for the site during compaction; and
h. a photoelectric sensor device used to determine soil material type at the x-y-z positions measured during compaction operations.

* * * * *